US010653695B2

(12) United States Patent
Alam et al.

(10) Patent No.: US 10,653,695 B2
(45) Date of Patent: May 19, 2020

(54) PHARMACEUTICAL FORMULATIONS OF NEFLAMAPIMOD

(71) Applicant: EIP Pharma, LLC, Cambridge, MA (US)

(72) Inventors: John Jahangir Alam, Cambridge, MA (US); Jeffrey Douglas Wilson, Vero Beach, FL (US)

(73) Assignee: EIP Pharma, LLC, Boston, MA (US)

( * ) Notice: Subject to any disclaimer, the term of this patent is extended or adjusted under 35 U.S.C. 154(b) by 0 days.

(21) Appl. No.: 16/351,448

(22) Filed: Mar. 12, 2019

(65) Prior Publication Data

US 2019/0275045 A1     Sep. 12, 2019

Related U.S. Application Data

(60) Provisional application No. 62/641,924, filed on Mar. 12, 2018.

(51) Int. Cl.
| | | |
|---|---|---|
| *A61K 31/519* | (2006.01) |
| *A61K 9/16* | (2006.01) |
| *A61K 9/48* | (2006.01) |
| *A61K 9/00* | (2006.01) |
| *A61K 47/26* | (2006.01) |
| *A61K 47/38* | (2006.01) |
| *A61K 47/12* | (2006.01) |

(52) U.S. Cl.
CPC .......... *A61K 31/519* (2013.01); *A61K 9/0053* (2013.01); *A61K 9/1617* (2013.01); *A61K 9/1623* (2013.01); *A61K 9/1652* (2013.01); *A61K 9/1682* (2013.01); *A61K 9/4858* (2013.01); *A61K 9/4866* (2013.01); *A61K 47/12* (2013.01); *A61K 47/26* (2013.01); *A61K 47/38* (2013.01)

(58) Field of Classification Search
CPC ........................... A61K 31/519; C07D 471/04
See application file for complete search history.

(56) References Cited

U.S. PATENT DOCUMENTS

| | | | | |
|---|---|---|---|---|
| 8,338,412 B2 * | 12/2012 | Bemis | ................. | C07D 213/56 514/233.2 |
| 2003/0135957 A1 * | 7/2003 | Phinney | ............... | C05G 3/0058 23/313 P |
| 2006/0193920 A1 | 8/2006 | Bosch et al. | | |
| 2016/0008364 A1 * | 1/2016 | Alam | ................... | A61K 31/519 514/248 |

FOREIGN PATENT DOCUMENTS

WO    WO-2019/056003 A1    3/2019

OTHER PUBLICATIONS

Rojas et al. AAPS PharmaSciTech, 2012, 13(4):1054-62.*
International Search Report for PCT/US2019/021930 (Pharmaceutical Formulations of Neflamapimod, filed Mar. 12, 2019), issued by ISA/US, 3 pages (May 10, 2019).
Written Opinion for PCT/US2019/021930 (Pharmaceutical Formulations of Neflamapimod, filed Mar. 12, 2019), issued by ISA/US, 8 pages (May 10, 2019).

* cited by examiner

*Primary Examiner* — Rei Tsang Shiao
(74) *Attorney, Agent, or Firm* — Wolf, Greenfield & Sacks, P.C.

(57) ABSTRACT

Disclosed are oral pharmaceutical compositions of neflamapimod that exhibit suitable exposure for administration in humans and/or that maintain a desirable dissolution profile under standard storage conditions.

17 Claims, 5 Drawing Sheets

FIG. 1 Overlay of Initial Neflamapimod Dissolution Profiles

FIG. 2A Overlay of Neflamapimod 40°C/75% RH Dissolution Profiles

FIG. 2B Overlay of Neflamapimod 60°C/Ambient RH Dissolution Profiles

FIG. 3A Neflamapimod Blend Processing Overlay T=0

FIG. 3B Neflamapimod Dissolution Results T = 2 Weeks

FIG. 4 Dissolution Comparison of Neflamapimod Capsules

PHARMACEUTICAL FORMULATIONS OF NEFLAMAPIMOD

CROSS REFERENCE TO RELATED APPLICATIONS

The present application claims the benefit of U.S. Provisional Application No. 62/641,924 filed Mar. 12, 2018, the entire content of which is herein incorporated by reference in its entirety.

BACKGROUND

Alzheimer's Disease (AD) is a degenerative brain disease and the most common cause of dementia. Dementia is a syndrome—a group of symptoms—that has a number of causes. The characteristic symptoms of dementia are difficulties with memory, language, problem-solving and other cognitive skills that affect a person's ability to perform everyday activities. These difficulties occur because nerve cells (neurons) in parts of the brain involved in cognitive function are dysfunctional, damaged or destroyed. Ultimately, as neuronal dysfunction and loss progresses, patients lose control over basic bodily functions such as walking and swallowing. Patients in the final stages of the disease are bedridden and require around-the-clock care. AD is ultimately fatal. (Alzheimer's Association, "2017 Alzheimer's Disease Facts and Figures", *Alzheimers Dement* 2017; 13:325-373). The estimated prevalence of AD in 2015 was more than 40 million patients worldwide, and it is estimated that this figure will be double by 2050. (J. K. Lee and N.-J. Kim, "Recent Advances in the Inhibition of p38 MAPK as a Potential Strategy for the Treatment of Alzheimer's Disease", *Molecules* 2017; 22:1287) ("Lee and Kim").

BRIEF SUMMARY

Five prescription drugs are currently approved by the U.S. Food and Drug Administration (FDA) for alleviating the symptoms of AD. Three of the five available medications— donepezil, galantamine and rivastigmine—belong to a class of drugs known as acetylcholinesterase (AchE) inhibitors. These drugs prevent the breakdown of acetylcholine, which is a neurotransmitter involved in learning and memory. The fourth drug is memantine, another class of AD drugs known as N-methyl-D-aspartic acid receptor (NMDAR) antagonists. Both types of drugs are prescribed to attenuate symptoms but work in different ways. The fifth drug is a combination of donepezil and memantine. These drugs help mask certain symptoms of AD but do not cure the disease or delay its progression. (Lee and Kim). Therefore, additional therapies are needed.

Neflamapimod (previously code-named VX-745) is a highly specific inhibitor of the intra-cellular enzyme p38 mitogen activated protein kinase alpha ("p38α"). (See, e.g., J. P. Duffy et al., "The Discovery of VX-745: A Novel and Selective p38r Kinase Inhibitor", *ACS Med Chem Lett* 2011; 2:758-763) ("Duffy"). Neflamapimod has very low solubility in water. (J. J. Haddad, "VX-745", *Curr Opin Invest Dugs* 2001; 2(8); 1070-1076). In order to obtain FDA approval of a solid oral dosage form, "a two-point dissolution specification—one at 15 minutes to include a dissolution range (a dissolution window) and the other at a later point (30, 45, or 60 minutes) to ensure 85% dissolution—is recommended to characterize the quality of the product. The product is expected to comply with dissolution specifications throughout its shelf life." (Center for Drug Evaluation and Research, *Guidance for Industry: Dissolution Testing of Immediate Release Solid Oral Dosage Forms*, August 1997.)

In some aspects, the present invention provides oral pharmaceutical compositions of neflamapimod that exhibit suitable exposure for administration in humans.

In some aspects, the present invention provides oral pharmaceutical compositions of neflamapimod that maintain a desirable dissolution profile under standard storage conditions.

In some aspects, the present invention provides methods of making oral pharmaceutical compositions of neflamapimod that exhibit suitable exposure for administration in humans and/or maintain a desirable dissolution profile under standard storage conditions, and the pharmaceutical compositions made by such methods.

In some aspects, the present invention provides dosage forms of neflamapimod that exhibit suitable exposure for administration in humans and/or maintain a desirable dissolution profile under standard storage conditions.

In some aspects, the present invention provides unit doses of neflamapimod that exhibit suitable exposure for administration in humans and/or maintain a desirable dissolution profile under standard storage conditions.

In some aspects, the present invention provides packaged dosage forms of neflamapimod that exhibit suitable exposure for administration in humans and/or maintain a desirable dissolution profile under standard storage conditions.

In some aspects, the present invention provides methods of treating Alzheimer's Disease in a subject in need thereof by orally administering a pharmaceutical composition of neflamapimod, a dosage form of neflamapimod, or one or more unit doses of neflamapimod.

DETAILED DESCRIPTION OF CERTAIN EMBODIMENTS

Definitions

As used herein, and unless otherwise specified, the terms "therapeutically effective amount" and "effective amount" of an agent (e.g., neflamapimod) refer to an amount sufficient to provide a therapeutic benefit in the treatment, prevention and/or management of a disease, disorder or condition, e.g., to delay onset of or minimize (e.g., reduce the incidence and/or magnitude of) one or more symptoms associated with the disease, disorder or condition to be treated. In some embodiments, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition. In some embodiments, a "therapeutically effective amount" is an amount that enhances therapeutic efficacy of another agent with which the composition is administered in combination.

The terms "treat" or "treating," as used herein, refer to partially or completely alleviating, inhibiting, delaying onset of or reducing the incidence of a disorder, disease or condition, or one or more symptoms or manifestations of the disorder, disease or condition.

The term "unit dose" as used herein refers to a physically discrete unit of a formulation appropriate for a subject to be treated (e.g., for a single dose), each unit containing a predetermined quantity of an active agent selected to produce a desired therapeutic effect when administered according to a therapeutic regimen (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described herein. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

References herein to "standard storage conditions" are based on current guidance from the International Conference on Harmonisation of Technical Requirements for Registration of Pharmaceuticals for Human Use ("ICH"), specifically, that storage for 6 months at 40° C./75% RH or 12 months at 30° C./65% RH is sufficiently predictive of long-term storage to be used as a proxy thereof.

Neflamapimod

Neflamapimod is the nonproprietary name adopted by the USAN council for the investigational drug previously code-designated VX-745. Neflamapimod is a brain-penetrant oral small molecule that inhibits the intra-cellular enzyme p38 mitogen activated protein kinase alpha ("p38 MAPKα"). The structure of neflamapimod is shown below:

Neflamapimod was originally in development to treat rheumatoid arthritis. (Duffy). More recently, neflamapimod has been studied for and in patients with early Alzheimer's Disease. (U.S. Pat. No. 8,697,627 (EIP Pharma); P. Scheltens et al., "Quantitative PET Study of the Effects of the p38α Kinase Inhibitor VX-745 on Brain Amyloid Plaque Load in Patients with Early Alzheimer's Disease (AD)", *J Prev Alz Dis* 2016; 3(Supp 1):272; J. Alam et al., "Clinical Pharmacology Study of p38 alpha Map Kinase Inhibitor, Neflamapomid (VX-745), in Mild Cognitive Impairment (MCI) Due to Alzheimer's Disease (AD) or Mild AD", *J Prev Alz Dis* 2016; 3(Supp 1):277-278; J. Alam et al., "Neflamapimod: Clinical Phase 2b-ready Oral Small Molecule Inhibitor of p38α to Reverse Synaptic Dysfunction in Early Alzheimer's Disease", *J Prev Alz Dis* 2017; 4(4):273-278; P. Scheltens et al., "p38α Kinase Inhibition Appears to Lead to Reduction in Amyloid-Beta Generation in Patients with Early Alzheimer's Disease", *J Prev Alz Dis* 2017; 4(4):389-390; J. Alam and C. Teunissen, "Demonstration of Blood-brain-barrier (BBB) Penetration and Brain Target Engagement for Neflamapimod (p38α Kinase Inhibitor) in Patients with Early Alzheimer's Disease (AD)", *J Prev Alz Dis* 2017; 4(4):390).

Exposure and Dissolution Studies of Pharmaceutical Compositions Containing Neflamapimod Exposure refers to the AUC (area under the curve) of average serum concentration of the species of interest (here, neflamapimod) plotted against time after administration and is a measure of the amount of the species absorbed into circulation following the administration. In prior clinical trials, in patients with rheumatoid arthritis (RA), various formulations of VX-745 (neflamapimod) were administered, including one containing micronized neflamapimod and microcrystalline cellulose (MMC), one containing micronized neflamapimod and lactose, and a proprietary nanoparticulate formulation developed by NanoSystems/Elan Pharma (see, e.g., Intl. Appl. Publ. No. WO 2003/080024). Exposure levels measured in those studies are shown in the following table.

TABLE 1

Exposure for various formulations and doses of neflamapimod

| Ind.* | Formulation/Dose | Steady-state AUC† | Dose-normalized AUC† (exposure per 100 mg dose administered) |
|---|---|---|---|
| RA | Neflamapimod/MMC (100 mg capsules)/ 500 mg BID‡ | 538 ng*hr/mL | 108 ng*hr/mL |

TABLE 1-continued

Exposure for various formulations and doses of neflamapimod

| Ind.* | Formulation/Dose | Steady-state AUC† | Dose-normalized AUC† (exposure per 100 mg dose administered) |
|---|---|---|---|
| RA | Micronized neflamapimod/lactose (125 mg capsules)/ 750 mg BID | 782 ng*hr/mL | 104 ng*hr/mL |
| RA | Nanoparticle neflamapimod (125 mg capsules)/ 250 mg BID | 453 ng*hr/mL | 181 ng*hr/mL |
| AD | Micronized neflamapimod/lactose (40 mg capsules)/ 40 mg BID | 78 ng*hr/mL | 195 ng*hr/mL |
| AD | Micronized neflamapimod/lactose (125 mg capsules)/ 125 mg BID | 116 ng*hr/mL | 93 ng*hr/mL |

*Indication: RA = rheumatoid arthritis; AD = early Alzheimer's Disease
†AUC = plasma VX-745 exposure over dosing interval
‡BID = bis in die (twice daily administration)

Phase 2a studies were conducted in patients with early Alzheimer's Disease, as described in Example 2.1. Patients received either 40 mg or 125 mg neflamapimod BID. In order to blind the study participants to the dose administered, the total weight of each dosage form was made the same. Accordingly, as the 125 mg capsule contained 254 mg lactose monohydrate (about 2:1 (w/w) diluent:micronized neflamapimod), the 40 mg capsule was made to contain about 339 mg lactose monohydrate (about 8.5:1 (w/w) diluent:micronized neflamapimod); all other components were present in equal amounts. Surprisingly, as shown in the table above, the capsules containing the larger ratio of diluent:micronized neflamapimod resulted in greater than 2:1 dose-normalized exposure. Without wishing to be bound by theory, the higher ratio of lactose to neflamapimod may facilitate and/or prolong maintenance of drug particles in a micronized state.

Figure 5:
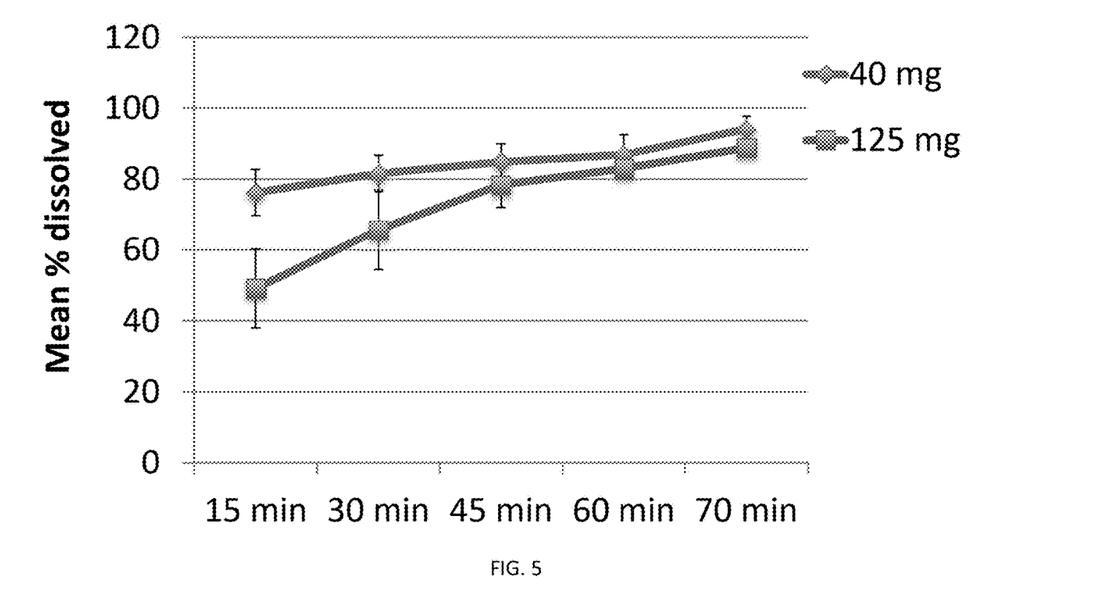
FIG. 5 shows dissolution profiles of 40 mg and 125 mg capsules described in Example 2.1 after storage for 1 month at room temperature (6 samples tested at each time point; error bars represent standard deviation).

Additionally, the capsules containing the larger ratio of diluent:micronized neflamapimod resulted in superior dissolution after 15 minutes, as shown in FIG. 5. Without wishing to be bound by theory, the increased dissolution may contribute to the greater exposure observed.

Additional data support the surprising nature of this observed phenomenon. One hypothesis posits that for a dissolution-limited molecule such as neflamapimod, a lower dose would be less affected by the dissolution limitation than a higher dose. That is, it could be that the higher dose formulation simply passes through the colon before being able to fully release and have the full dose be absorbed. However, if that were the case one would expect that an even larger dose would result in no further increase in exposure (or, at a minimum, even a further blunting of dose-normalized exposure); and as shown it Table 1, that is not what is observed. Instead, administration of 125 mg capsules of micronized neflamapimod in a lactose formulation at 750 mg BID resulted in a steady-state AUC more than 6 times greater than that observed after administration of 125 mg BID (782 ng*hr/mL vs. 116 ng*hr/mL).

Figure 6:
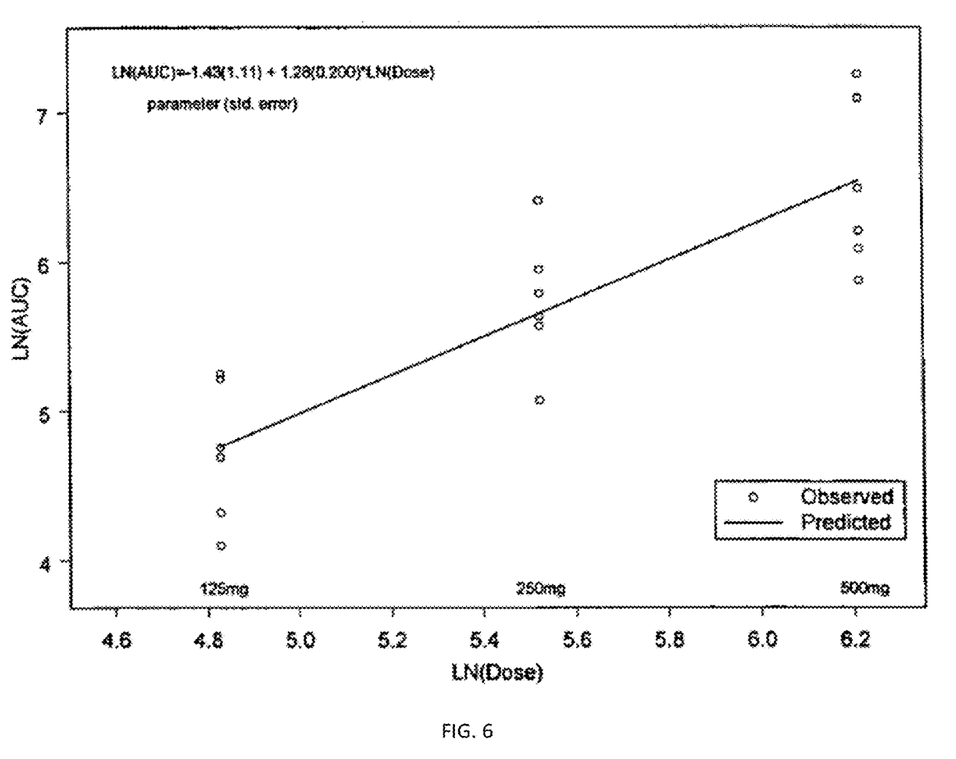
FIG. 6 shows a plot of ln(AUC) against ln(dose) after administration of 125 mg capsules of micronized neflamapimod in a lactose formulation to healthy volunteers.

Dose-proportionality studies of neflamapimod further support the unexpected nature of this finding. Three different doses of 125 mg capsules of micronized neflamapimod in a lactose formulation—125 mg, 250 mg and 500 mg—were administered to healthy volunteers. As shown in FIG. 6, the increase in AUC with increasing dose can be described with the following equation: $\ln(AUC)=-1.43+1.28*\ln(dose)$, where "ln" indicates the natural logarithm of the expression that follows it. Notably, the equation predicts an AUC of 116 ng*hr/mL for a dose of 125 mg, which was observed in the AD study mentioned above (see Table 1). Moreover, the equation predicts an AUC of 27 ng*hr/mL for a dose of 40 mg, nearly three times lower than the 78 ng*hr/mL observed with the formulation provided by the present invention.

Dissolution on Stability Studies of Neflamapimod Drug Product

USP Dissolution Acceptance Criteria. Dissolution testing of a drug product is a method for evaluating physiological availability that depends upon having the drug in a dissolved state. The United States Pharmacopoeia ("USP") dissolution testing <USP 711> involves three stages with the acceptance criteria defined for each stage as a function of a quantity Q, a percentage of the label value that is established for each drug product. USP dissolution acceptance criteria for neflamapimod are shown in Table 2 below.

TABLE 2

USP Dissolution Acceptance Criteria

| Stage | Number Units Tested | Acceptance Criteria |
|---|---|---|
| S1 | 6 | Each unit is not less than Q* + 5% |
| S2 | 6 | Average of the 12 (S1 + S2) units is ≥ Q, and no unit is less than Q − 15% |
| S3 | 12 | Average of the 24 (S1 + S2 + S3) units is ≥ Q, no more than 2 units are less than Q − 15%, and no unit is less than Q − 25% |

*Q is the amount of dissolved active ingredient specified in the individual monograph, expressed as a percentage of the labeled content. For neflamapimod, Q = 75% of label claim at 60 minutes.

Figure 1:
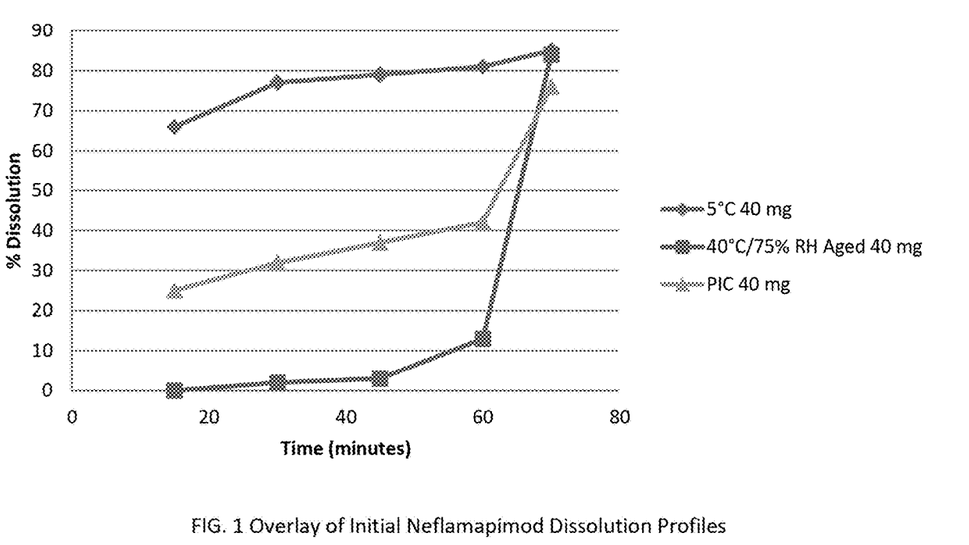
FIG. 1 shows dissolution profiles of neflamapimod capsules under stressed and unstressed conditions compared to powder-in-capsule.

Initial Testing. As shown in FIG. 1, 40 mg neflamapimod capsules after storage under stressed conditions (40° C./75% RH) exhibited a deterioration in dissolution compared to capsules stored at 5° C., and even as compared to samples of powder-in-capsule ("PIC").

It was observed in the 40° C./75% RH samples that although the capsule shell had substantially eroded by the 45-minute time point the slug of formulation inside the capsule was mostly intact. The formulated 40 mg capsules from both conditions reached almost the same level of dissolution at the final infinity time point. The rapid release of neflamapimod concurrent with increase in paddle speed at the infinity time point coupled with the observations of a slug present at earlier time points suggested a formulation disintegration issue in the stressed capsules.

Figure 2A:
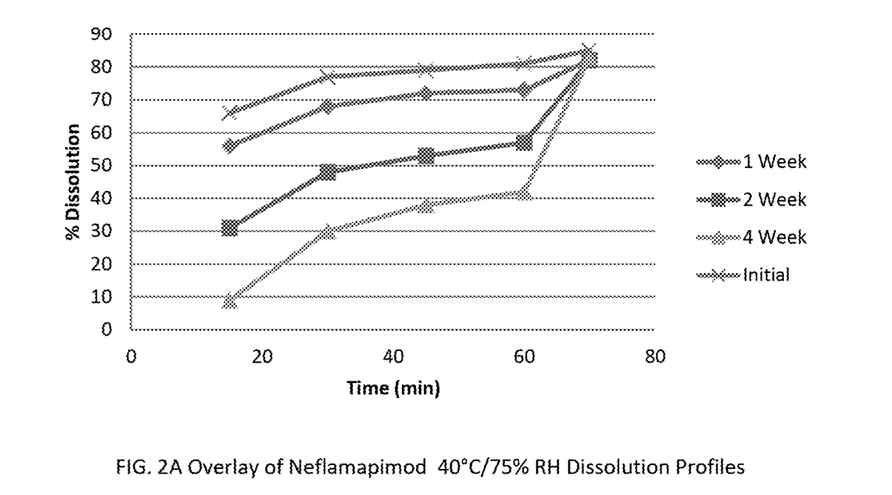
FIGS. 2A and 2B show dissolution profiles of neflamapimod capsules on open dish stability at 40° C./75% RH (2A) and 60° C./ambient RH (2B).
Figure 2B:
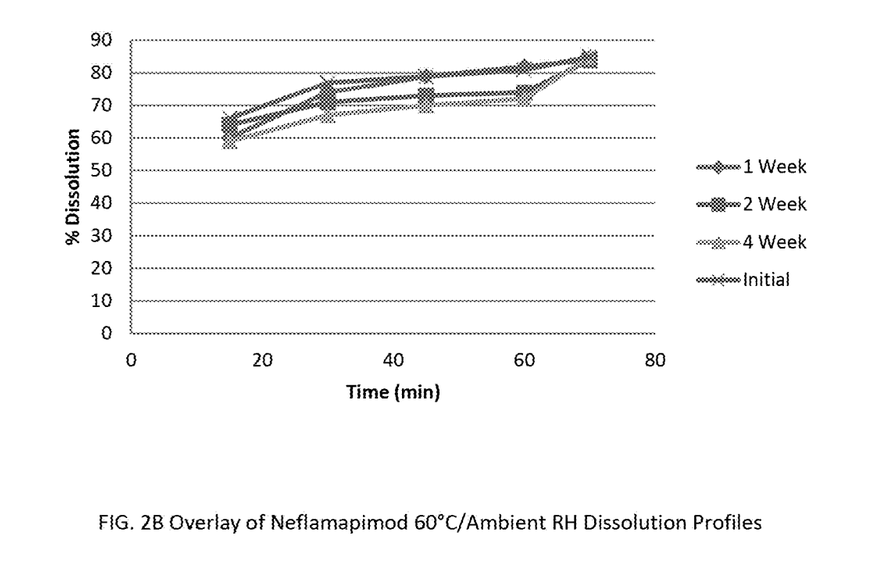

Moisture vs. Temperature. In order to determine whether the impaired dissolution after storage under stressed conditions was due to temperature or moisture and temperature, 40 mg neflamapimod capsules were placed on open dish stability at 40° C./75% RH and 60° C./ambient RH and analyzed after 1, 2 and 4 weeks. As shown in FIGS. 2A and 2B, the 60° C. ambient/RH samples showed substantially less slowing in dissolution than the 40° C./75% RH stressed samples. This indicated that the exposure to moisture and temperature had a more substantial effect on dissolution than the exposure to elevated temperature alone.

Amorphous Content. Analysis by DSC (differential scanning calorimetry) had suggested a higher content of amorphous neflamapimod in capsules stored at 5° C. compared to those stored under stressed conditions (as evidenced by differences in enthalpy) and the possibility of a recrystallization event (as evidenced by the presence of an exothermic peak at 168° C.). In order to investigate the source and effect of amorphous content and recrystallization on dissolution, a simple blend and dry granulation of the neflamapimod 40 mg formulation were generated on a small scale. The preparation of a simple blend and dry granulation were intended to isolate the manufacturing process and help determine if the wet granulation procedure could be enhancing dissolution and generating the amorphous content. These blends were analyzed at time (T)=0 by dissolution and DSC, and were then placed on accelerated stability open at 40° C./75% RH along with neflamapimod wet-granulated capsules and analyzed at T=2 weeks.

Figure 3A:
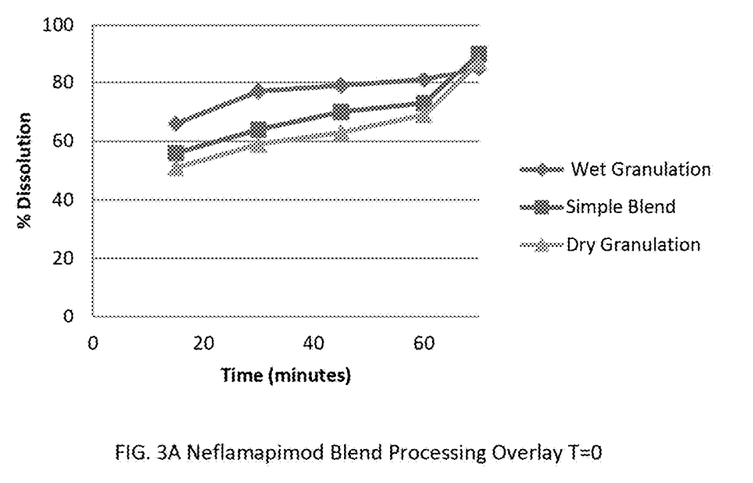
FIGS. 3A and 3B show dissolution profiles of neflamapimod simple blend, dry granulation and wet granulation initially (3A) and after 2 weeks (3B) under accelerated stability (open at 40° C./75% RH).
Figure 3B:
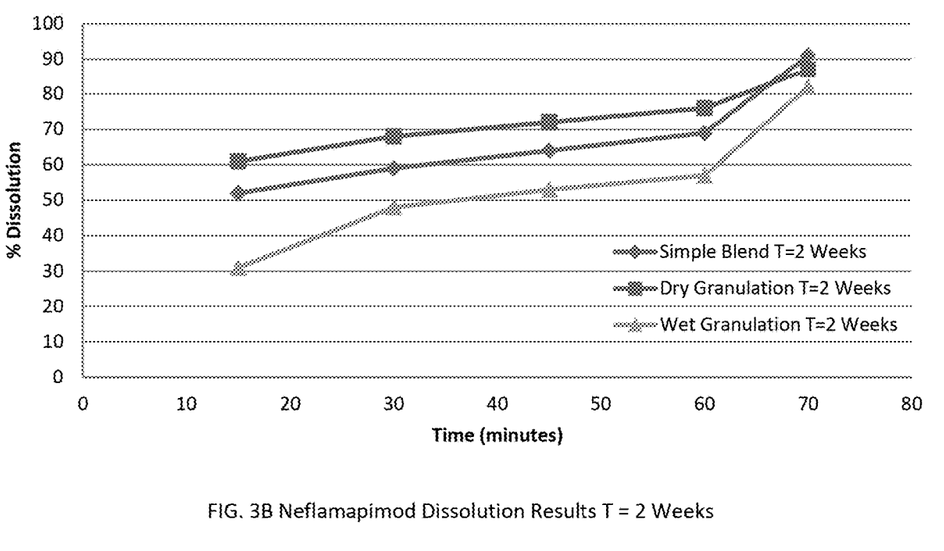

Analysis by DSC dry samples at T=0 and T=2 weeks showed no substantial appearance of the exothermic peak, while after 2 weeks a substantial exothermic peak at 167° C. was still present in the wet-granulated capsule. As shown in FIGS. 3A and 3B, dissolution of neither dry blend was substantially slowed after 2 weeks of accelerated stability. Neither the simple blend nor the dry granulation showed the same marked decrease in dissolution as the wet granulation after 2 weeks under accelerated conditions. This suggested that the amorphous content was not entirely responsible for the slowing of dissolution rate.

Packaging Configurations. The effects of different packaging configurations on the dissolution slowing seen in neflamapimod capsules were evaluated to determine whether alternative packaging configurations could alleviate the drop in dissolution seen at accelerated conditions. Neflamapimod 40 mg capsules were packaged in a 60 cc HDPE (high-density polyethylene) bottle with desiccant, a foil pouch, and a foil pouch with desiccant. These were then stored at 40° C./75% RH for 3 months. At 3 months, samples from each packaging configuration were evaluated by dissolution and DSC.

Figure 4:
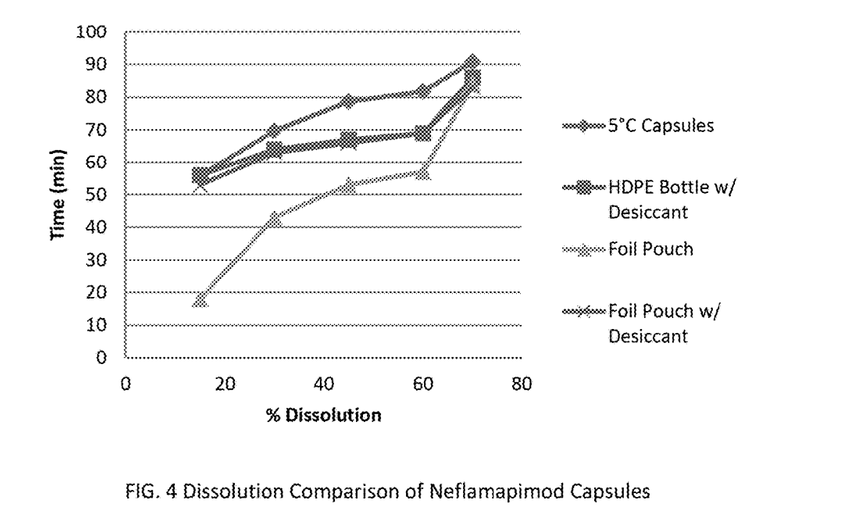
FIG. 4 shows dissolution profiles under stressed conditions (40° C./75% RH for 3 months) of neflamapimod capsules stored in HDPE bottles with desiccant, foil pouches with desiccant and foil pouches with desiccant compared to unstressed (5° C.) capsules.

As shown in FIG. 4, the neflamapimod capsules stored in desiccated HDPE bottles and desiccated foil pouches showed better dissolution than the neflamapimod capsules stored in foil pouches without desiccant. However, all samples showed slowed dissolution relative to unstressed (5° C.) capsules. The DSC thermograms of all samples were very similar, and an exothermic peak at 166° C. was present at only a minimal level. The results of this study suggest that desiccation inhibited the effect of moisture on dissolution rate. However, it appears that both exposure to heat and moisture affect the dissolution of neflamapimod capsules inasmuch as slowing was observed in all packaging configurations.

Conclusions. The observed decrease in dissolution rate can likely be attributed to two separate sources. The first source is loss of the enhancement that is generated by the wet granulation and the complete or partial neflamapimod form change from crystalline to amorphous. As illustrated in FIG. 3A, a simple blend and dry granulation underperform relative to the wet granulation material at T=0. This demonstrates that the wet granulation, and presumed amorphous content, enhance the dissolution rate. After storage at accelerated temperature in a dry environment, the materials revert back to the non-enhanced rate which is represented by the dry blend dissolution profile. This decrease is correlated with a reduction in the exothermic DSC event, indicating a loss of the amorphous content.

The second source is a decrease in disintegration rate over prolonged storage in humid conditions. This is likely due to moisture ingress and slugging of the filler (in these capsules, lactose) with neflamapimod. Dissolution suppression due to poor formulation disintegration is illustrated in FIG. 1, where better dissolution is seen with unformulated crystalline neflamapimod than the aged capsules. This indicated that the decreased dissolution is due to the formulation or manufacturing process rather than neflamapimod's intrinsic dissolution rate. Finally, the additional dissolution rate suppression of non-desiccated samples versus those stored in a dry environment, illustrated in FIGS. 2A, 2B and 4, indicate water ingress as the cause.

It has now been discovered that neflamapimod can be formulated with a water-containing diluent, and drug products containing such formulations of neflamapimod can be produced and packaged, such that a desirable dissolution profile is maintained under standard storage conditions.

Pharmaceutical Compositions of Neflamapimod

In some aspects, the present invention provides an oral pharmaceutical composition of neflamapimod that exhibits suitable exposure for administration in humans. In some embodiments, the pharmaceutical composition comprises neflamapimod and a diluent, wherein the ratio of diluent to neflamapimod (w/w) is about 6:1 to about 12:1. In some embodiments, the ratio of diluent to neflamapimod is about 7:1 to about 10:1. In some embodiments, the ratio of diluent to neflamapimod is about 8:1 to about 9:1.

Formulations of the present invention contain neflamapimod. In all formulations of the present invention, references to neflamapimod are to micronized neflamapimod, whether or not modified by the term "micronized".

In some embodiments, a pharmaceutical composition comprises neflamapimod and a diluent, wherein the ratio of diluent to neflamapimod is about 6:1 to about 12:1 (w/w), about 7:1 to about 10:1, or about 8:1 to about 9:1, and the diluent comprises lactose, preferably lactose monohydrate. In some embodiments, a pharmaceutical composition comprises neflamapimod and a diluent, wherein the ratio of diluent to neflamapimod is about 6:1 to about 12:1 (w/w), about 7:1 to about 10:1, or about 8:1 to about 9:1, and the diluent consists essentially of lactose, preferably lactose monohydrate.

In some aspects, the present invention provides an oral pharmaceutical composition of neflamapimod that maintains a desirable dissolution profile under standard storage conditions. In some aspects, the invention provides a granular pharmaceutical composition comprising neflamapimod and a diluent, wherein the average moisture level (measured according to the procedure of Example 1.3) of the granules is less than 4.0% (w/w). In some embodiments, the moisture level of the granules is about 0.1% to less than 4.0%, about 0.5% to less than 4.0%, about 1.0% to less than 4.0%, about 1.5% to less than 4.0%, about 2.0% to less than 4.0%, about 2.5% to less than 4.0%, about 0.1% to about 3.5%, about 0.5% to about 3.5%, about 1.0% to about 3.5%, about 1.5% to about 3.5%, about 2.0% to about 3.5%, or about 2.5% to about 3.5%.

A diluent is a substance used to increase the bulk of a composition to make it a practical size (e.g., for handling, compression, etc.). Diluents suitable for use in the pharmaceutical compositions of the present invention include calcium carbonate, confectioner sugar, cellulose, silicified cellulose, calcium phosphate dibasic, calcium phosphate tribasic, calcium phosphate anhydrous, calcium hydrogen phosphate dihydrate, ethyl cellulose, lactose anhydrous, lactose monohydrate, microcrystalline cellulose, mannitol, methyl cellulose, magnesium carbonate, magnesium oxide, pregelatinized starch, starch (e.g., potato, corn, wheat, rice), sucrose, sodium chloride and talc. In some embodiments, a diluent comprises a disaccharide. In some embodiments, a diluent comprises lactose. In some embodiments, the diluent comprises lactose monohydrate. In some embodiments, the diluent consists essentially of lactose monohydrate.

Pharmaceutical compositions of the present invention can contain one of more additional excipients, such as disintegrants, lubricants, anticaking agents, binders, antioxidants, glidants and preservatives (e.g., antimicrobial preservatives).

Disintegrants are substances used to facilitate the disintegration of a composition following administration. Disintegrants suitable for use in the pharmaceutical compositions of the present invention include alginic acid, citric acid, croscarmellose sodium, colloidal silicon dioxide, microcrystalline cellulose, powdered cellulose, carboxymethylcellulose calcium, crospovidone, polyvinylpyrrolidone (povidone), sodium starch glycolate, pregelatinized starch, starch (e.g., potato, corn, wheat, rice), sodium alginate and sodium carboxymethylcellulose.

Lubricants are substances used to prevent adhesion of a composition to machine surfaces, reduce interparticle friction and/or improve the rate of flow of a composition granulation. Lubricants suitable for use in the pharmaceutical compositions of the present invention include calcium stearate, hydrogenated castor oil, glyceryl monostearate, glyceryl behenate, magnesium stearate, polyethylene glycol, Polaxamer 407, Polaxamer 188, sodium lauryl sulfate, sodium benzoate, stearic acid, sodium stearyl fumarate and talc.

Anticaking agents are substances used to prevent the formation of lumps (caking) in a composition. Anticaking agents suitable for use in the pharmaceutical compositions of the present invention include colloidal silicon dioxide, calcium phosphate dibasic, calcium phosphate tribasic and talc.

Binders are substances used to impart cohesive qualities to a composition. Binders suitable for use in the pharmaceutical compositions of the present invention include acacia, alginate, alginic acid, candelilla wax, carnuba wax, corn starch, copolyvidone, ethyl cellulose, gelatin, glyceryl behenate, hydroxypropyl cellulose, hydroxypropyl methylcellulose, lactose anhydrous, lactose monohydrate, methyl cellulose, polyvinylpyrrolidone (povidone), polyethylene oxide, pregelatinized starch, starch (e.g., potato, corn, wheat, rice), sodium alginate and sodium carboxymethylcellulose.

Antioxidants are substances used to inhibit the oxidation of other substances (e.g., the active agent) in a composition. Antioxidants suitable for use in the pharmaceutical compositions of the present invention include butylated hydroxy toluene.

Glidants are substances used to improve flow characteristics of a powder composition. Glidants suitable for use in the pharmaceutical compositions of the present invention include colloidal silicon dioxide, cellulose, calcium phosphate dibasic, calcium phosphate tribasic, magnesium stearate, pregelatinized starch, starch (e.g., potato, corn, wheat, rice) and talc.

Due to the overlap in function between some excipients, it is not always possible (or necessarily meaningful) to ascribe a function exclusively to a particular excipient type. For example, in formulations of the present invention, magnesium stearate may be referred to variously as a lubricant or a glidant without any intended difference in the constitution of the formulation.

Preservatives are substances used to prevent decomposition of other substances (e.g., the active agent) in a composition by microbial growth or chemical change. Preservatives suitable for use in the pharmaceutical compositions of the present invention include antimicrobial preservatives such as benzyl alcohol, butyl paraben, cetylpyridine chloride, glycerin, methyl paraben, propylene glycol, propylene paraben, potassium sorbate, sodium benzoate, sorbic acid and sodium propionate.

In some embodiments, a pharmaceutical composition comprises neflamapimod; a diluent, wherein the diluent consists essentially of lactose, preferably lactose monohydrate, and wherein the ratio (w/w) of diluent to neflamapimod is about 8:1 to about 9:1; a disintegrant, preferably croscarmellose sodium; a binder, preferably polyvinylpyrrolidone; and a lubricant, preferably magnesium stearate.

In some embodiments, a pharmaceutical composition comprises neflamapimod; a diluent, wherein the diluent consists essentially of lactose monohydrate, and wherein the ratio (w/w) of diluent to neflamapimod is about 8:1 to about 9:1; a disintegrant comprising croscarmellose sodium; a binder comprising polyvinylpyrrolidone; and a lubricant comprising magnesium stearate.

In some embodiments, a pharmaceutical composition comprises neflamapimod; a diluent, wherein the diluent consists essentially of lactose monohydrate, and wherein the ratio (w/w) of diluent to neflamapimod is about 8:1 to about 9:1; a disintegrant consisting essentially of croscarmellose sodium; a binder consisting essentially of polyvinylpyrrolidone; and a lubricant consisting essentially of magnesium stearate.

In some embodiments, a pharmaceutical composition consists essentially of neflamapimod; a diluent, wherein the diluent consists essentially of lactose monohydrate, and wherein the ratio (w/w) of diluent to neflamapimod is about 8:1 to about 9:1; a disintegrant consisting essentially of croscarmellose sodium; a binder consisting essentially of polyvinylpyrrolidone; and a lubricant consisting essentially of magnesium stearate.

Methods of Making Pharmaceutical Compositions of Neflamapimod

In some aspects, the invention provides a method of making the above pharmaceutical compositions comprising the following steps: wet-granulating a mixture comprising neflamapimod and a diluent to form granules; and drying the granules until the moisture level is less than 4.0% (w/w).

Wet granulation is process that is well known in the art. Wet granulation is the process of binding different powder particles together using adhesives or liquid solution (the granulating solution) to form granules. Any suitable method of wet granulation can be used to make the granulated compositions described herein, e.g., fluid bed granulation, high shear granulation. Any suitable granulating solution can be used to make the granulated compositions described herein, e.g., a mixture of a solvent such as water and a binder such as polyvinylpyrrolidone.

In some embodiments, the granules are dried to a moisture level of about 0.1% to about 4.0%, about 0.5% to less than 4.0%, about 1.0% to less than 4.0%, about 1.5% to less than 4.0%, about 2.0% to less than 4.0%, about 2.5% to less than 4.0%, about 0.1% to about 3.5%, about 0.5% to about 3.5%, about 1.0% to about 3.5%, about 1.5% to about 3.5%, about 2.0% to about 3.5%, or about 2.5% to about 3.5%.

Additional steps that can be employed in the wet granulation process are within the scope of the method. For example, in a typical granulation, micronized neflamapimod is sifted together with diluent (such as lactose monohydrate) and disintegrant (such as croscarmellose sodium) through a mesh screen. Solvent (such as water) and binder (such as polyvinylpyrrolidone) are then used in the granulation step.

Any method suitable for drying granules that achieves the desired moisture level is suitable for use in the method. In some embodiments, the granules are dried using a fluid bed dryer.

In some aspects, the invention provides a pharmaceutical composition comprising neflamapimod and a diluent as described herein, made according to the wet granulation process described herein. In some embodiments, the invention provides a pharmaceutical composition comprising neflamapimod and a diluent as described herein, made according to the wet granulation process described herein, wherein the granulating solution preferably comprises a solvent, preferably water, and a binder, preferably polyvinylpyrrolidone. In some such embodiments, a pharmaceutical composition further comprises one or more excipients, each of which independently is intragranular or extragranular. In some such embodiments, a pharmaceutical composition made according to the wet granulation process described herein further comprises an intragranular disintegrant, preferably croscarmellose sodium. In some such embodiments, a pharmaceutical composition made according to the wet granulation process described herein further comprises an extragranular lubricant, preferably magnesium stearate. In some such embodiments, a pharmaceutical composition made according to the wet granulation process described herein further comprises an intragranular disintegrant, preferably croscarmellose sodium, and an extragranular lubricant, preferably magnesium stearate.

Dosage Forms of Neflamapimod

In some aspects, the present invention provides a pharmaceutical composition of neflamapimod as described herein in a dosage form suitable for administration. Many dosage forms are well known in the art. See, e.g., REMINGTON: THE SCIENCE AND PRACTICE OF PHARMACY, $20^{th}$ ed., A. R. Gennaro (ed.), Lippincott Williams & Wilkins: Baltimore (2000), incorporated herein by reference in its entirety. Any orally administrable dosage form is suitable for use with the pharmaceutical composition. In some embodiments, a dosage form is a tablet, capsule or powder. In some embodiments, the dosage form is a capsule.

Unit Doses of Neflamapimod

In some aspects, the invention provides a unit dose of a neflamapimod-containing dosage form as described herein. In some embodiments, a unit dose comprises (1) about 38 mg to about 42 mg neflamapimod and about 320 mg to about 360 mg lactose monohydrate; (2) about 40 mg neflamapimod and about 330 mg to about 350 mg lactose monohydrate; or (3) about 40 mg neflamapimod and about 335 mg to about 345 mg lactose monohydrate. In some embodiments, a unit dose is in the form of a capsule and comprises (1) about 38 mg to about 42 mg neflamapimod and about 320 mg to about 360 mg lactose monohydrate; (2) about 40 mg neflamapimod and about 330 mg to about 350 mg lactose monohydrate; or (3) about 40 mg neflamapimod and about 335 mg to about 345 mg lactose monohydrate.

In some embodiments, a unit dose comprises (1) about 38 mg to about 42 mg neflamapimod, about 320 mg to about 360 mg lactose monohydrate, about 10 mg to about 18 mg disintegrant, preferably croscarmellose sodium, about 12 mg to about 24 mg binder, preferably polyvinylpyrrolidone, and about 1 mg to about 3 mg lubricant, preferably magnesium stearate; (2) about 40 mg neflamapimod, about 330 mg to about 350 mg lactose monohydrate, about 10 mg to about 18 mg disintegrant, preferably croscarmellose sodium, about 12 mg to about 24 mg binder, preferably polyvinylpyrrolidone, and about 1 mg to about 3 mg lubricant, preferably magnesium stearate; or (3) about 40 mg neflamapimod, about 335 mg to about 345 mg lactose monohydrate, about 12 mg to about 16 mg disintegrant, preferably croscarmellose sodium, about 14 mg to about 22 mg binder, preferably polyvinylpyrrolidone, and about 1.5 mg to about 2.5 mg lubricant, preferably magnesium stearate. In some such embodiments, a unit dose is in the form of a capsule.

Packaged Drug Products Containing Neflamapimod

In some aspects, the invention provides a packaged neflamapimod-containing drug product as described herein that maintains a desirable dissolution profile and/or maintains a desirable moisture content under standard storage conditions. In some embodiments, a packaged neflamapimod-containing drug product maintains a desirable dissolution profile under standard storage conditions. In some embodiments, a packaged neflamapimod-containing drug product maintains a desirable moisture content under standard storage conditions.

In some embodiments, a packaged neflamapimod-containing drug product comprises unit doses of neflamapimod as described herein packaged in double low density polyethylene (LDPE) bags placed in high density polyethylene (HDPE) drums, wherein there is at least one bag of desiccant between the inner and outer bags and at least one bag of desiccant between the outer bag and the drum. In some embodiments, the packaged unit doses of neflamapimod are further packaged in humidity-resistant packaging, such as blister packs comprising cold formable laminate and aluminum foil blister lidding.

As illustrated in Example 1.2, packaged drug product in accordance with the present invention exhibits dissolution that satisfies USP acceptance criteria after at least 6 months of accelerated storage conditions. In some embodiments, accelerated storage conditions are 25° C./60% RH. In some embodiments, accelerated storage conditions are 30° C./65% RH. In some embodiments, accelerated storage conditions are 40° C./75% RH.

EXAMPLES

Example 1.1. Dissolution Testing Parameters

Dissolution testing data described herein are generated according to the specifications shown below in Table 3 and using the procedure set forth by the United States Pharmacopeial Convention in USP <711>.

TABLE 3

| Dissolution testing parameters | |
|---|---|
| Parameter | Condition |
| Instrument | Distek Dissolution Bath, or equivalent |
| Vessel Volume | 1000 mL |
| Media | 1.5% SLS in 25 mM Ammonium Acetate Buffer, pH 4.0, with Pepsin |
| Media Volume | 900 mL |
| Number of Units | n = 3 |
| Temperature | 37.0 ± 0.5° C. |
| Apparatus | USP Apparatus 2, Paddles with Sinkers |
| Speed | 50 ± 2 RPM, 250 ± 10 RPM (∞) (Paddles) |
| Time Points | 15, 30, 45, 60 and 70(∞) minutes |
| Theoretical Concentration | 44.444 µg/mL (40 mg Capsules) |

Example 1.2. Dissolution of Neflamapimod Drug Product Stored in Foil-Blister Packaging with Desiccant Determined by the procedure set forth in Example 1.1. Results are shown below in Table 4.

TABLE 4

Dissolution following different storage conditions

% Label Claim Dissolved After 60 Minutes

| Storage Conditions | Foil-blister Packaging with Desiccant | | | | | Packaging without Desiccant | | |
| --- | --- | --- | --- | --- | --- | --- | --- | --- |
| | T = 0 | 1 Mo. | 2 Mos. | 3 Mos. | 6 Mos. | T = 0 | 4 Mos. | 7 Mos. |
| 25° C. 60% RH | 96 | 97 | 90 | 95 | 96 | 93 | 86 | 88 |
| 30° C. 65% RH | NT | 95 | 96 | 98 | 94 | NT | 89 | 83 |
| 40° C. 75% RH | NT | 91 | 81 | 81 | 82 | NT | 71 | NT |

NT = not tested

Example 1.3. Moisture Assay (Karl Fischer)

Standardize the Karl Fischer apparatus (values shown herein were generated using an Orion Turbo 2 Blending Karl Fischer). Weigh five capsules and record the total weight. Empty the contents of the capsules into a suitable container and record the weight of the empty capsule shells. Calculate the average capsule fill weight as shown below.

$$\text{Average Capsule Fill Weight (mg)} = \frac{\text{Total Capsule Weight (mg)} - \text{Empty Capsule Weight (mg)}}{5 \text{ capsules}}$$

Mix the sample composite well using a clean spatula. Transfer the equivalent of the average, enter the weight in the instrument in grams, and transfer the equivalent of the average capsule fill weight into a pre-titrated vessel and titrate to end-point using 30 second stir time and the instrumental settings listed below. Perform in duplicate from the same sample composite.

Titrant: HYDRANAL Composite 5
Solvent: Methanol
Stir Time: 30 seconds

Example 2.1. Phase 2a Clinical Trial Study Designs

A total of 25 patients were enrolled in two studies: 16 in Study 302 (9 at 40 mg and 7 at 125 mg for 12 weeks), and 9 in Study 303 (8 at 40 mg and 1 at 125 mg for up to 6 weeks).

Study 302 (12-week treatment). Sixteen patients (aged 60 to 85 years) with MCI due to AD or mild AD were randomized on a blinded basis to 40 mg or 125 mg neflamapimod twice daily with food for 12 weeks. The main efficacy endpoint was a change in amyloid load as measured quantitatively using dynamic [$^{11}$C]-PiB ("Pittsburgh-B") PET scans, performed at baseline and at end of treatment (Day 84), analyzed by reference parametric mapping (RPM2) using cerebellum as reference tissue (Yaqub et al, 2008). As the quantitative dynamic approach to PET scanning reduces test-retest variability to 2-3%, the pre-specified responder definition was a >7% reduction in PET signal. Secondary outcome measures included change in Wechsler Memory Scale (WMS) and Mini-Mental-Status-Examination (MMSE).

Study 303 (6-week treatment). Patients with MCI due to AD or mild AD and an MRI consistent with AD were included. Originally, 16 patients were to be randomized to either 40 mg or 125 mg neflamapimod twice daily with food for six weeks. However, after 3 subjects were enrolled, the higher dose group was discontinued due to US-specific regulatory authority requirement to limit dosing to expected plasma drug exposure levels providing ten-fold safety margin relative to long-term animal toxicology findings. Cerebrospinal fluid (CSF) cytokines and AB peptides were assessed at Baseline and at week 6 (end-of-treatment), and intensive plasma and CSF pharmacokinetics obtained on Days 1 and 41. Verbal learning/episodic memory was assessed with the Hopkins Verbal Learning Test-Revised (HVLT-R). MMSE was evaluated at screening and Day 40.

What is claimed is:

1. A pharmaceutical composition suitable for oral administration, comprising:
    neflamapimod; and
    lactose,
    wherein the ratio (w/w) of lactose to neflamapimod is about 8:1.
2. The pharmaceutical composition of claim 1, further comprising a disintegrant.
3. The pharmaceutical composition of claim 2, wherein the disintegrant comprises croscarmellose sodium.
4. The pharmaceutical composition of claim 1, further comprising a lubricant.
5. The pharmaceutical composition of claim 4, wherein the lubricant comprises magnesium stearate.
6. The pharmaceutical composition of claim 5, in the form of granules.
7. A pharmaceutical composition in the form of granules, wherein:
    the granules comprise neflamapimod and lactose, wherein the ratio (w/w) of lactose to neflamapimod is about 8:1; and
    the moisture level of the granules is less than 4.0% (w/w).
8. The pharmaceutical composition of claim 7, further comprising a disintegrant.
9. The pharmaceutical composition of claim 8, wherein the disintegrant comprises croscarmellose sodium.
10. The pharmaceutical composition of claim 7, further comprising one or more extragranular excipients.
11. The pharmaceutical composition of claim 10, wherein the one or more extragranular excipients comprises a lubricant.
12. The pharmaceutical composition of claim 11, wherein the lubricant comprises magnesium stearate.
13. A dosage form suitable for oral administration, comprising the pharmaceutical composition of claim 1.
14. The dosage form of claim 13, wherein the dosage form is a capsule.

15. A unit dose of the dosage form of claim 14, wherein the amount of neflamapimod is about 38 mg to about 42 mg.

16. A packaged drug product comprising the dosage form of claim 15, and humidity-resistant packaging.

17. A method of making the pharmaceutical composition of claim 10, comprising the steps of:
- wet-granulating a mixture comprising neflamapimod and lactose to form granules; and
- drying the granules until the moisture level is less than 4.0% (w/w).

* * * * *